United States Patent
Lim et al.

(10) Patent No.: US 6,562,080 B2
(45) Date of Patent: May 13, 2003

(54) PRIMARY INTERMEDIATES FOR OXIDATIVE COLORATION OF HAIR

(75) Inventors: Mu-Ill Lim, Trumbull, CT (US); Yuh-Guo Pan, Stamford, CT (US)

(73) Assignee: Clairol Incorporated, Stamford, CT (US)

( * ) Notice: Subject to any disclaimer, the term of this patent is extended or adjusted under 35 U.S.C. 154(b) by 0 days.

(21) Appl. No.: 09/930,651

(22) Filed: Aug. 15, 2001

(65) Prior Publication Data

US 2002/0144355 A1 Oct. 10, 2002

Related U.S. Application Data

(60) Provisional application No. 60/229,182, filed on Aug. 30, 2000.

(51) Int. Cl.$^7$ .................................................. A61K 7/13
(52) U.S. Cl. ................. 8/405; 8/405; 8/406; 8/407; 8/408; 8/409; 8/412; 8/421; 564/307; 564/324; 546/290; 546/246; 546/312
(58) Field of Search ............................ 8/405, 406, 407, 8/408, 409, 412, 421; 564/307, 324; 546/290, 296, 312

(56) References Cited

U.S. PATENT DOCUMENTS 4,797,130 A * 1/1989 Clausen et al. ................ 8/421

* cited by examiner

*Primary Examiner*—Yogendra N. Gupta
*Assistant Examiner*—Eisa Elhilo
(74) *Attorney, Agent, or Firm*—Charles J. Zeller

(57) ABSTRACT

Primary intermediates useful hair coloring systems comprise 2-arylaminomethyl-4-aminophenols. The invention provides new 2-arylaminomethyl-4-aminophenol compounds of Formula (1):

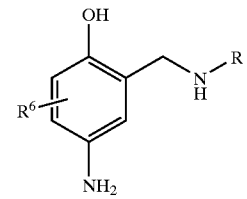

(1)

wherein R is a moiety selected from formulae (2), (3) or (4)

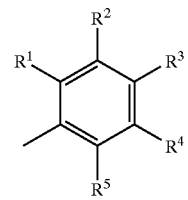

(2)

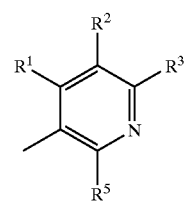

(3)

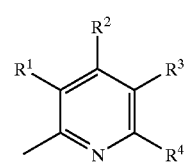

(4)

wherein $R^1$, $R^2$, $R^3$, $R^4$ and $R^5$ are each independently selected from a hydrogen atom, a halogen atom, a hydroxy group, an amino group, a $C_1$–$C_6$ alkyl or haloalkyl group, a $C_1$–$C_6$ alkoxy or haloalkoxy group, and a nitrile group, and $R^6$ is a hydrogen atom, a halogen atom, a $C_1$–$C_4$ alkyl or a $C_1$–$C_4$ alkoxy group.

27 Claims, No Drawings

PRIMARY INTERMEDIATES FOR OXIDATIVE COLORATION OF HAIR

This application claims the benefit of Application No. 60/229,182, filed Aug. 30, 2000.

FIELD OF THE INVENTION

This invention relates to new 2-arylaminomethyl-4-aminophenol compounds and compositions containing these compounds as primary intermediates for oxidative coloring of hair fibers.

BACKGROUND OF THE INVENTION

Coloration of hair is a procedure practiced from antiquity employing a variety of means. In modem times, the method most extensively to color hair is an oxidative dyeing process utilizing one or more oxidative hair coloring agents in combination with one or more oxidizing agents.

Most commonly a peroxy oxidizing agent is used in combination with one or more oxidative hair coloring agents, generally small molecules capable of diffusing into hair and comprising one or more primary intermediates and one or more couplers. In this procedure, a peroxide material, such as hydrogen peroxide, is employed to activate the small molecules of primary intermediates so that they react with couplers to form larger sized complexes in the hair shaft to color the hair in a variety of shades and colors.

A wide variety of primary intermediates and couplers have been employed in such -oxidative hair coloring systems and compositions. Among the primary intermediates employed there may be mentioned p-phenylenediamine, p-toluenediamine, p-aminophenol, 4-amino-3-methyl-phenol, N,N-bis(2-hydroxyethyl)-p-phenylenediamine, 1-(2-hydroxyethyl)-4,5-diaminopyrazole and as couplers there may be mentioned resorcinol, 2-methylresorcinol, 3-aminophenol, 2,4-diaminophenoxyethanol, and 5-amino-2-methylphenol.

There are numerous additional requirements for oxidation dye compounds that are used to dye human hair besides the color or the desired intensity. Thus, the dye compounds must be unobjectionable in regard to toxicological and dermatological properties and must provide the desired hair color with a good light fastness, fastness to a permanent wave treatment, acid fastness and fastness to rubbing. The color of the hair dyed with the dye compounds in each case must be stable for at least 4 to 6 weeks to light, rubbing and chemical agents. Furthermore, an additional requirement is the production of a broad palette of different color shades using different developer and coupler substances. It is not possible to fulfill all the above-mentioned requirements with the currently known dye compounds. There is, therefore, a need for new primary intermediate compounds to meet one or more of the desired properties.

SUMMARY OF THE INVENTION

It is therefore an object of this invention to provide new primary intermediate compounds useful in place of p-aminophenol to provide a wide range of different color shades with various combinations of primary intermediates and couplers.

It has been discovered that new 2-arylaminomethyl-4-aminophenol compounds are suitable primary intermediates for hair coloring compositions and systems for providing good oxidative coloration of hair and for providing acceptable light fastness, fastness to shampooing, fastness to permanent wave treatment, and suitable for providing a wide variety of different color shades with various primary intermediate and coupler compounds.

The invention provides new 2-arylaminomethyl-4-aminophenol compounds of Formula (1):

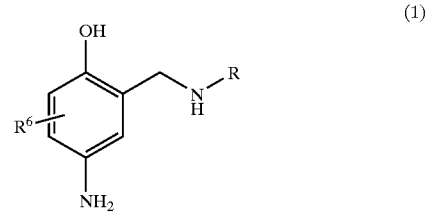

(1)

wherein R is a moiety selected from formulae (2), (3) or (4)

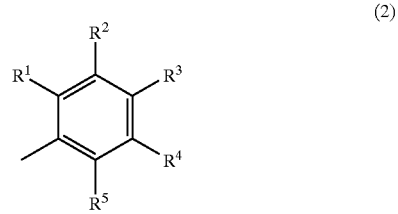

(2)

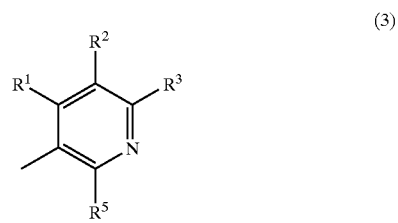

(3)

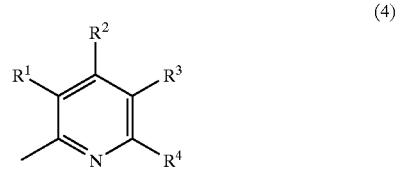

(4)

wherein $R^1$, $R^2$, $R^3$, $R^4$ and $R^5$ are each independently selected from a hydrogen atom, a halogen atom, a hydroxy group, an amino group, a $C_1$–$C_6$ alkyl or haloalkyl group, a $C_1$–$C_6$ alkoxy or haloalkoxy group, and a nitrile group, and $R^6$ is a hydrogen atom, a halogen atom, a $C_1$–$C_4$ alkyl or a $C_1$–$C_4$ alkoxy group.

Preferably $R^6$ is hydrogen; $R^1$ and $R^5$ are each independently hydrogen methyl, ethyl, methoxy, ethoxy, or chlorine; $R^2$ and $R^4$ are each independently hydrogen, chlorine, fluorine, methyl, ethyl, methoxy, trifluoromethyl, or trifluoromethoxy; and $R^3$ is hydrogen, hydroxy, fluorine, methyl, ethyl, propyl, methoxy, ethoxy or trifluoromethyl.

The new 2-arylaminomethyl-4-aminophenols of this invention can be made in a solid-phase organic synthesis reaction process utilizing a brominated Wang resin according to the following reaction scheme where R and $R^6$ are as defined hereinbefore.

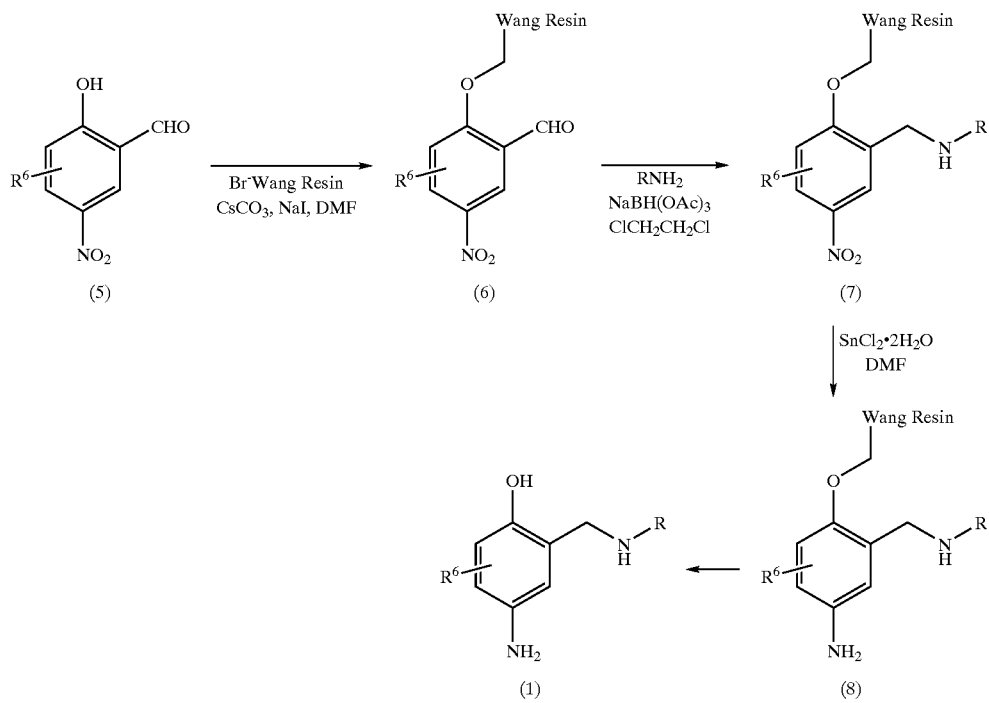

In a first step 2-hydroxy-5-nitrobenzaldehyde is attached to a brominated polystyrene Wang resin as follows.

A mixture of 4-(bromomethyl)phenoxymethyl polystyrene (40.22 g, 51.48 mmole, Wang bromopolystyrene, 1.28 mmole/g, Novabiochem®), 2-hydroxy-5-nitrobenzaldehyde of Formula (5) (43.45 g, 26 mmole) where $R^6$ represents hydrogen, cesium carbonate (50.83 g, 156 mmole), and sodium iodide (7.79 g, 52 mmole) in dimethylformamide (DMF) (350 mL) was stirred at 50° C. for 5 h. The resin was filtered and washed with 2:1 DMF/water (×3), 9:1 DMF/water (×3), DMF (×3) and alternating MeOH and dichloromethane (DCM) (×4). After drying under high vacuum overnight, the polymer-bound aldehyde of Formula (6) (42.748 g) was obtained. To determine the bonding of benzaldehyde onto the Wang resin, to determine molarity for subsequent reactions, the cleavage of resin (500 mg of the polymer-bound aldehyde) was carried out by treatment with 50% trifluroacetic acid (TFA)/DCM (5/5 mL) for 1.5 h at room temperature and filtered, washed with DCM and concentrated to give 2-hydroxy-5-nitrobenzaldehyde of Formula (5) (73.2 mg). Therefore, loading was determined to be 0.876 mmole/g.

After attachment of 2-hydroxy-5-nitrobenzaldehyde to the brominated Wang resin, the following is the general procedure for preparation of arylaminomethyl-aminophenol compounds of Formula (1).

Polymer bound nitrobenzaldehyde of Formula (6) ($R^6$=H) (300 mg, 0.263 mmole) was then treated with an aromatic amine of the formula $RNH_2$ (1.315 mmole each) in 1% AcOH-DCE (dichloroethane) (9 mL). A polypropylene tube (10 mL reservoir) was used as a reaction vessel in a 48-vessel reactor block. An orbital shaker was used for agitation. The mixture was agitated for 1 h at room temperature and sodium triacetoxyborohydride (1.315 mmole, 5 equiv.) was added to each reaction well. The mixture was agitated for 23 h. The solvent was filtered and the same washing protocol described above was followed. The resin was dried under vacuum overnight to give compound of Formula (7). The resin was treated with a 0.438 M $SnCl_2$ $2H_2O$ solution (6 mL, 10 equiv.) in DMF and the mixture was shaken for 24 h at room temperature. After the filtration of the solvent, the resin was washed three times each with DMF and alternating MeOH and DCM (×3). The resin was dried under vacuum overnight to afford a compound of Formula (8). The resin was cleaved with 5 mL of 50% TFA/DCM at room temperature for 1.5 h. After collection of the filtrate, the resin was washed with 1 mL of TFA/DCM and the combined filtrate was concentrated in vacuum to yield the target compound of Formula (1). The crude product was purified by preparative RP-HPLC using a gradient of 10% MeOH—90% $H_2O$—0.1% TFA (A) and 90% MeOH—10% $H_2O$—0.1% TFA (B) with a flow rate of 30 mL/min and gradient time 6 min. Start % B is 6 and final % B is 100. Evaporation of the solvents gives the target compounds of Formula (1).

Among the compounds of Formula (1) of this invention that can be prepared according to the aforedescribed general synthesis method, there can be mentioned, for example, 4-amino-2-phenylaminomethyl-phenol; 4-amino-2-[(3-chloro-phenylamino)-methyl]-phenol; 4-amino-2-[(4-fluoro-phenylamino)-methyl phenol; 4-amino-2-[(2-ethoxy-phenylamino)-methyl]-phenol; 4-amino-2-[(4-ethoxy phenylamino)-methyl]-phenol; 4-amino-2-[(3-fluoro-4-methoxy-phenylamino)-methyl]phenol; 4-amino-2-[(3-methoxy-phenylamino)-methyl]-phenol; 4-amino-2-[(3,4dimethyl-phenylamino)-methyl]-phenol; 4-amino-2-[(3-fluoro-phenylamino)-methyl]phenol; 4-amino-2-[(2-methoxy-5-methyl-phenylamino)-methyl]-phenol; 4-amino-2[(4-methoxy-2-methyl-phenylamino)-methyl]-phenol; 4-amino-2-[(5-methoxy methyl-phenylamino)-methyl]-phenol; 3-(5-amino-2-hydroxy-benzylamino benzonitrile; 4-amino-2-[(3-trifluoromethyl-phenylamino)-methyl]-phenol; 4-amino-2[(4-trifluoromethyl-phenylamino)-methyl]-phenol; 4-amino-2-[(4,6-dimethyl-pyridin-2ylamino)-methyl]-phenol; 4-amino-2-[(3,4-dimethoxy-phenylamino)-methyl]-phenol 4-amino-2-[(4-hydroxyphenylamino)-methyl]-phenol; 4-amino-2-[(4-ethyl-phenyl amino)-methyl]-phenol; 4-amino-2-[(4-hydroxy-2,5-dimethyl-phenylamino)-methyl phenol; 4-amino-2-[(4-methoxy-phenylamino)-methyl]-phenol; 4-amino-2-[(2-chloro phenylamino)-methyl]-phenol; 4-amino-2-[(3-fluoro-4-methoxy-phenylamino)-methyl phenol; 4-amino-2-[(3-trifluoromethoxy-phenylamino)-methyl]-phenol; 4-amino-2-(p tolylamino-methyl)-phenol; 4-amino-2-(o-tolylamino-methyl)phenol; 4-amino-2-[(2methoxy-phenylamino)-methyl]-phenol; 4-amino-2-(m-tolylamino-methyl)-phenol; 4amino-2-[(4-propyl-phenylamino)-methyl]-phenol; 4-amino-2-[(2,3-dimethyl-phenyl amino)-methyl]-phenol; 4-amino-2-[(2,5-dimethyl-phenylamino)-methyl]-phenol; 4amino-2-[(3,5-dimethyl-phenylamino)-methyl]-phenol; 4-amino-2-[(2-ethyl-phenyl amino)-methyl]-phenol; 4-amino-2-[(3-ethyl-phenylamino)-methyl]-phenol; 4-amino-2(pyridin-3-ylaminomethyl)-phenol; 5-methyl-4-amino-2-phenylaminomethyl-phenol; 5 methyoxy-4-amino-2-phenylaminomethyl-phenol; 5-chloro-4-amino-2-phenylamino methyl-phenol; 4-amino-2-[(2-fluoro-phenylamino)-methyl]-phenol; 4-amino-2-[(2hydroxy-phenylamino)-methyl]-phenol; 4-amino-2-[2-amino-phenylamino)-methyl phenol; 4-amino-2-[(2-trifluoromethyl-phenylamino)-methyl]-phenol; 4-amino-2-[(2-trifluoromethoxy-phenylamino)-methyl]-phenol; 2-(5-amino-2-hydroxy-benzylamino)-benzonitrile; 4-(5-amino-2-hydroxy-benzylamino)-benzonitrile; 4-amino-2-[(4-amino-phenylamino)-methyl]-phenol; 4-amino-2-[(4-chloro-phenylamino)-methyl]-phenol; and 4-amino-2-[(4-trifluoromethoxy-phenylamino)-methyl]-phenol.

The 2-arylaminomethyl-4-aminophenol compounds of Formula (1) can be employed in dye compositions and systems of this invention in an amount of from about 0.005 to about 20, preferably from about 0.01 to about 5.0, and most preferably from about 0.1 to about 2.5 weight percent based on the weight of the hair coloring composition.

Although advantageous properties of the above-described 2-arylaminomethyl-4-aminophenol compounds of Formula (I) can be obtained when they are employed as the sole primary intermediate in hair coloring compositions or systems of this invention, it is to be recognized that these compounds of Formula (I) may be employed together with one or more other suitable primary intermediates.

Examples of such other suitable primary intermediates include: p-phenylenediamine derivatives such as: benzene-1,4-diamine, 2-methyl-benzene-1,4-diamine, 2-chloro-benzene-1,4-diamine, N-phenyl-benzene-1,4-diamine, N-(2-ethoxyethyl)benzene-1,4-diamine, 2-[(4-amino-phenyl)-(2-hydroxy-ethyl)-amino]-ethanol, (2,5-diamino-phenyl)-methanol, 1-(2,5-diamino-phenyl)-ethanol, 2-(2,5-diamino-phenyl)ethanol, N-(4-aminophenyl)benzene-1,4-diamine, 2,6-dimethyl-benzene-1,4-diamine, 2-isopropyl-benzene-1,4-diamine, 1-[(4-aminophenyl)amino]propan-2-ol, 2-propyl-benzene-1,4-diamine, 1,3-bis[(4-aminophenyl)(2-hydroxyethyl)amino]propan-2-ol, $N^4,N^4,2$-trimethylbenzene-1,4-diamine, 2-methoxy-benzene-1,4-diamine, 1-(2,5-diaminophenyl)ethane-1,2-diol, 2,3-dimethyl-benzene-1,4-diamine, N-(4-amino-3-hydroxy-phenyl)-acetamide, 2,6-diethylbenzene-1,4-diamine, 2,5-dimethylbenzene-1,4-diamine, 2-thien-2-ylbenzene-1,4-diamine,2-thien-3-ylbenzene-1,4-diamine, 2-pyridin-3-ylbenzene-1,4-diamine, 1,1'-biphenyl-2,5-diamine, 2-(methoxymethyl)benzene-1,4-diamine, 2-(aminomethyl)benzene-1,4-diamine, 2-(2,5-diaminophenoxy)ethanol, N-[2-(2,5-diaminophenoxy)ethyl]acetamide, N,N-dimethylbenzene-1,4-diamine, N,N-diethylbenzene-1,4-diamine, N,N-dipropylbenzene-1,4-diamine, 2-[(4-aminophenyl)(ethyl)amino]ethanol, 2-[(4-amino-3-methyl-phenyl)-(2-hydroxy-ethyl)-amino]-ethanol, N-(2-methoxyethyl)benzene-1,4-diamine, 3-[(4-aminophenyl)amino]propan-1-ol, 3-[(4-aminophenyl)amino]propane-1,2-diol, N-{4-[(4-aminophenyl)amino]butyl}benzene-1,4-diamine, and 2-[2-(2-{2-[(2,5-diaminophenyl)oxy]ethoxy}ethoxy)ethoxy]benzene-1,4-diamine;

p-aminophenol derivatives such as: 4-amino-phenol, 4-methylamino-phenol, 4-amino-3-methyl-phenol, 4-amino-2-hydroxymethyl-phenol, 4-amino-2-methyl-phenol, 4-amino-2-[(2-hydroxy-ethylamino)-methyl]-phenol, 4-amino-2-methoxymethyl-phenol, 5-amino-2-hydroxy-benzoic acid, 1-(5-amino-2-hydroxy-phenyl)-ethane-1,2-diol, 4-amino-2-(2-hydroxy-ethyl)-phenol, 4-amino-3-(hydroxymethyl)phenol, 4-amino-3-fluoro-phenol, 4-amino-2-(aminomethyl)phenol, and 4-amino-2-fluoro-phenol;

o-aminophenol derivatives such as: 2-amino-phenol, 2,4-diaminophenol, 2-amino-5-methyl-phenol, 2-amino-6-methyl-phenol, N-(4-amino-3-hydroxy-phenyl)-acetamide, and 2-amino4-methyl-phenol; and heterocyclic derivatives such as: pyrimidine-2,4,5,6-tetramine, 1-methyl-1H-pyrazole-4,5-diamine, 2-(4,5-diamino-1 H-pyrazol-1-yl)ethanol, $N^2,N^2$-dimethyl-pyridine-2,5-diamine, 2-[(3-amino-6-methoxypyridin-2-yl)amino]ethanol, 6-methoxy-N2-methyl-pyridine-2,3-diamine, 2,5,6-triaminopyrimidin-4(1H)-one, pyridine-2,5-diamine, 1-isopropyl-1H-pyrazole-4,5-diamine, 1-(4-methylbenzyl)-1H-pyrazole-4,5-diamine, and 1-(4-chlorobenzyl)-1H-pyrazole4,5-diamine.

The primary intermediates can be employed in the form of a free base or in the form of an acid additive salt thereof, such as, for example, as a hydrochloride, a hydrobromide, a sulfate or the like.

The 2-arylaminomethyl-4-aminophenol compounds of Formula (1) alone or in combination with such other suitable primary intermediates may be employed in hair coloring compositions or systems of this invention with any suitable coupler. The coupler compounds can be employed in the hair coloring compositions or systems of this invention in an amount of from about 0.005 to about 20, preferably from about 0.01 to about 5.0, and most preferably from about 0.1 to about 2.5 weight percent based on the total weight of the hair coloring composition.

Suitable couplers include, for example, phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, 7-amino4-hydroxy-naphthalene-2-sulfonic acid, 2-isopropyl-5-methylphenol, 1,2,3,4-tetrahydro-naphthalene-1,5-diol, 2-chloro-benzene-1,3-diol, 4-hydroxy-naphthalene-1-sulfonic acid, benzene-1,2,3-triol, naphthalene-2,3-diol, 5-dichloro-2-methylbenzene-1,3-diol, 4,6-dichlorobenzene-1,3-diol, and 2,3-dihydroxy-[1,4] naphthoquinone;

m-phenylenediamines such as: 2,4-diaminophenol, benzene-1,3-diamine, 2-(2,4-diamino-phenoxy)-ethanol, 2-[(3-amino-phenyl)-(2-hydroxy-ethyl)-amino]-ethanol, 2-methyl-benzene-1,3-diamine, 2-[[2-(2,4-diamino-phenoxy)-ethyl]-(2-hydroxy-ethyl)-amino]-ethanol, 4-{3-[(2,4-diaminophenyl)oxy]propoxy}benzene-1,3-diamine, 2-(2,4-diamino-phenyl)-ethanol, 2-(3-amino-4-methoxy-phenylamino)-ethanol, 4-(2-amino-ethoxy)-benzene-1,3-diamine, (2,4-diamino-phenoxy)-acetic acid, 2-[2,4- diamino-5-(2-hydroxy-ethoxy)-phenoxy]-ethanol, 4-ethoxy-6-methyl-benzene-1,3-diamine, 2-(2,4-diamino-5-methyl-phenoxy)-ethanol, 4,6-dimethoxybenzene-1,3-diamine, 2-[3-(2-hydroxy-ethylamino)-2-methyl-phenylamino]-ethanol, 3-(2,4-diamino-phenoxy)-propan-1-ol, N-[3-(dimethylamino)phenyl]urea, 4-methoxy-6-methylbenzene-1,3-diamine, 4-fluoro-6-methylbenzene-1,3-diamine, 2-({3-[(2-hydroxyethyl)amino]-4,6-dimethoxy-phenyl}amino)ethanol, 3-(2,4-diaminophenoxy)propane-1,2-diol, 2-[2-amino-4-(methylamino)phenoxy]ethanol, 2-[(5-amino-2-ethoxy-phenyl)-(2-hydroxy-ethyl)-amino]-ethanol, 2-[(3-aminophenyl)amino]ethanol N-(2-aminoethyl)benzene-1,3-diamine, 4-{[(2,4-diaminophenyl)oxy]methoxy}benzene-1,3-diamine, and 2,4-dimethoxybenzene-1,3-diamine;

m-aminophenols such as: 3-amino-phenol, 2-(3-hydroxy-4-methyl-phenylamino)-acetamide, 2-(3-hydroxy-phenylamino)-acetamide, 5-amino-2-methyl-phenol, 5-(2-hydroxy-ethylamino)-2-methyl-phenol, 5-amino-2,4-dichloro-phenol, 3-amino-2-methyl-phenol, 3-amino-2-chloro-6-methyl-phenol, 5-amino-2-(2-hydroxy-ethoxy)-phenol, 2-chloro-5-(2,2,2-trifluoro-ethylamino)-phenol, 5-amino-4-chloro-2-methyl-phenol, 3-cyclopentylamino-phenol, 5-[(2-hydroxyethyl)amino]4-methoxy-2-methylphenol, 5-amino-4-methoxy-2-methylphenol, 3-(dimethylamino)phenol, 3-(diethylamino)phenol, 5-amino-4-fluoro-2-methylphenol, 5-amino-4-ethoxy-2-methylphenol, 3-amino-2,4-dichloro-phenol, 3-[(2-methoxyethyl)amino]phenol, 3-[(2-hydroxyethyl)amino]phenol, 5-amino-2-ethyl-phenol, 5-amino-2-methoxyphenol, 5-[(3-hydroxypropyl)amino]-2-methylphenol, 3-[(3-hydroxy-2-methylphenyl)-amino]propane-1,2-diol, and 3-[(2-hydroxyethyl)amino]-2-methylphenol; and heterocyclic derivatives such as: 3,4-dihydro-2H-1,4-benzoxazin-6-ol, 4-methyl-2-phenyl-2,4-dihydro-3H-pyrazol-3-one, 6-methoxyquinolin-8-amine, 4-methylpyridine-2,6-diol, 2,3-dihydro-1,4-benzodioxin-5-ol, 1,3-benzodioxol-5-ol, 2-(1,3-benzodioxol-5-ylamino)ethanol, 3,4-dimethylpyridine-2,6-diol, 5-chloropyridine-2,3-diol, 2,6-dimethoxypyridine-3,5-diamine, 1,3-benzodioxol-5-amine, 2,6-bis(2-hydroxyethoxy)-3,5-diaminopyridine, 1H-indol-4-ol, 5-amino-2,6-dimethoxypyridin-3-ol, 1H-indole-5,6-diol, 1H-indol-7-ol, 1H-indol-5-ol, 1H-indol-6-ol, 6-bromo-1,3-benzodioxol-5-ol, 2-aminopyridin-3-ol, pyridine-2,6-diamine, 3-[(3,5-diaminopyridin-2-yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine, and 3,4-dihydro-2H-1,4-benzoxazin-6-amine.

Preferred primary intermediates include:

p-phenylenediamine derivatives such as: 2-methyl-benzene-1,4-diamine, benzene-1,4-diamine, 1-(2,5-diamino-phenyl)-ethanol, 2-(2,5-diamino-phenyl)-ethanol, N-(2-methoxyethyl)benzene-1,4-diamine, 2-[(4-amino-phenyl)-(2-hydroxy-ethyl)-amino]-ethanol, and 1-(2,5-diaminophenyl)ethane-1,2-diol;

p-aminophenol derivatives such as 4-amino-phenol, 4-methylamino-5 phenol, 4-amino-3-methyl-phenol, 4-amino-2-methoxymethyl-phenol, and 1-(5-amino-2-hydroxy-phenyl)-ethane-1,2-diol;

o-aminophenol derivatives such as: 2-amino-phenol, 2-amino-5-methyl-phenol, 2-amino-6-methyl-phenol, N-(4-amino-3-hydroxy-phenyl)-acetamide, and 2-amino4-methyl-phenol;

heterocyclic derivatives such as: pyrimidine-2,4,5,6-tetramine, 1-methyl-1H-pyrazole-4,5-diamine, 2-(4,5-diamino-1H-pyrazol-1-yl)ethanol, and $N^2,N^2$-dimethyl-pyridine-2,5-diamine.

Preferred couplers include:

phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, and 2-isopropyl-5-methylphenol;

m-phenylenediamines such as: benzene-1,3-diamine, 2-(2,4-diamino-phenoxy)-ethanol, 4-{3-[(2,4-diaminophenyl)oxy]propoxy}benzene-1,3-diamine, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol;

m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one, 1,3-benzodioxol-5-ol, 1,3-benzodioxol-5-amine, 1H-indol-4-ol, 1H-indole-5,6-diol, 1H-indol-7-ol, 1H-indol-5-ol, 1H-indol-6-ol, 1H-indole-2,3-dione, pyridine-2,6-diamine, and 2-aminopyridin-3-ol.

Most preferred primary intermediates include:

p-phenylenediamine derivatives such as: 2-methyl-benzene-1,4-diamine, benzene-1,4-diamine, 2-(2,5-diamino-phenyl)-ethanol, 1-(2,5-diamino-phenyl)-ethanol, and 2-[(4-amino-phenyl)-(2-hydroxy-ethyl)-amino]-ethanol;

p-aminophenol derivatives such as: 4-amino-phenol, 4-methylamino-phenol, 4-amino-3-methyl-phenol, and 1-(5-amino-2-hydroxy-phenyl)-ethane-1,2-diol;

o-aminophenols such as: 2-amino-phenol, 2-amino-5-methyl-phenol, 2-amino-6-methyl-phenol, and N-(4-amino-3-hydroxy-phenyl)-acetamide; and heterocyclic derivatives such as: pyrimidine-2,4,5,6-tetramine and 2-(4,5-diamino-1H-pyrazol-1-yl)ethanol.

Most preferred couplers include:

phenols, resorcinol and naphthol derivatives such as: benzene-1,3-diol, 4-chlorobenzene-1,3-diol, naphthalen-1-ol, 2-methyl-naphthalen-1-ol, and 2-methyl-benzene-1,3-diol;

m-phenylenediamine such as: 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)propan-1-ol;

m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one,and 1H-indol-6-ol, and 2-aminopyridin-3-ol.

The total amount of the combination of primary intermediate and coupler compounds in the hair coloring compositions or systems of this invention is generally from about 0.001 to about 10, preferably from about 0.02 to about 10 and most preferably from about 0.2 to about 6.0 weight percent based on the total weight of the hair coloring composition. The primary intermediate and coupler compounds are generally used in equivalent amounts. However, it is possible to use the primary intermediate compounds in either excess or deficiency.

The hair coloring compositions according to the invention can also contain certain other dye ingredients, for example Acid Orange 3, Disperse Orange 3, Disperse Black 9, HC Orange 1, HC Orange 2, HC Orange 3, HC Yellow 2, HC Yellow 4, HC Yellow 5, HC Yellow 6, HC Yellow 7, HC Yellow 9, HC Yellow 10, HC Yellow 11, HC Yellow 12, HC Yellow 13, HC Yellow 14, HC Yellow 15, 4-nitro-o-phenylenediamine, 2-nitro-5-glyceryl methylaniline, 4-nitrophenyl aminoethylurea, hydroxyethyl-2-nitro-p-toluidine, 3-methylamino-4-nitrophenoxyethanol, 2-amino-6-chloro-4-nitrophenol, 2-chloro-6-ethylamino-4-nitrophenol, Basic Yellow 57, Solvent Orange 45, 4-nitro-m-phenylenediamine, Natural Orange 6, 2-hydroxyethylamino-5-nitroanisole, 2-amino-3-nitrophenol, 6-nitro-o-toluidine, N-ethyl-3-nitro PABA, N-hydroxyethyl-2,6-dinitro-p-anisidine, 6-nitro-2,5-pyridinediamine, 4-chloro-5-methyl-2-nitrophenol HC Red 1, HC Red 3, HC Red 7, HC Red 10, HC Red 11, HC Red 13, HC Red 14, 2-nitro-p-henylenediamine, 3-nitro-p-hydroxyethylaminophenol, 4-hydroxypropyl-amino-3-nitrophenol, 4-amino-3-nitrophenol, picramic acid, N-(2-hyroxyethyl)picramic acid, Basic Red 76, Disperse Red 17, N-methyl-3-nitro-p-phenylenediamine, 2-chloro-5-nitro-N-hydroxyethyl-p-phenylenediamine, 4-amino-2-nitrodiphenylamine-2'-carboxylic acid, 4-amino-4'-dimethylamino-2-nitrodiphenylamine-2'-carboxylic acid Disperse Violet 1, Disperse Violet 4, HC Blue 2, HC Blue 6, HC Blue 9, HC Blue 10, HC Blue 11, HC Blue 12, HC Violet 1, HC Violet 2, N,N'-bis(2-hydroxyethyl)-2-nitro-p-phenylenediamine, 2-nitro4-[bis(2-hydroxyethyl)amino]diphenylamine, Basic Violet 14

Disperse Blue 1, Disperse Blue 3, Basic Blue 7, Basic Blue 9, Basic Blue 26, Basic Blue 17, Basic Blue 99

Basic Brown 16, Basic Brown 17, Acid Black 1.

These dye compounds can be contained in the hair coloring composition of the invention in an amount of from about 0.1 to 4.0 percent by weight.

Understandably, the coupler compounds and the primary intermediate compounds, as well as the other dye compounds, in so far as they are bases, can also be used in the form of their physiologically compatible salts with organic or inorganic acids, such as hydrochloric acid or sulfuric acid, or, in so far as they have aromatic OH groups, in the form of their salts with bases, such as alkali phenolates.

Moreover, cosmetic additive ingredients, which are commonly used in compositions for coloring hair, can be used in the hair coloring compositions according to the invention, for example antioxidants, such as ascorbic acid, thioglycolic acid or sodium sulfite, and perfume oils, complex formers, wetting agents, emulsifiers, thickeners and care materials.

The form of the hair coloring compositions according to the invention can be, for example, a solution, especially an aqueous or aqueous-alcoholic solution. However, the form that is particularly preferred is a cream, gel or an emulsion. Its composition is a mixture of the dye ingredients with the conventional cosmetic additive ingredients suitable for the particular preparation.

Conventional cosmetic additive ingredients in solutions, creams, emulsion or gels include, for example, solvents, such as water, lower aliphatic alcohols, such as ethanol, propanol or isopropanol, glycerol or glycols, such as 1,2-propylene glycol; wetting agents or emulsifiers from the classes of anionic, cationic, amphoteric or nonionic surfactant compounds, such as fatty alcohol sulfates, ethoxylated fatty alcohol sulfates, alkylsulfonates, alkylbenzensulfonates, alkyltrimethylammonium salts, alkylbetaines, ethoxylated fatty alcohols, ethoxylated nonylphenols, fatty acid alkanol amides and ethoxylated fatty acid esters; thickeners, such as higher fatty alcohols, starches, cellulose derivatives, petrolatum, paraffin oil, fatty acids and anionic and nonionic polymeric thickeners based on polyacrylic and polyurethane polymers, e.g., Aculyn sold by Rohm & Haas, as well as care materials, such as cationic resins, lanolin derivatives, cholesterol, pantothenic acids and betaine. The above-mentioned conventional cosmetic ingredients are used in amounts suitable for their purposes. For example the wetting agents and emulsifiers are used in concentrations of from about 0.5 to 30 percent by weight, the thickeners are used in an amount of from about 0.1 to 25 percent by weight and the care materials are used in concentrations of from about 0.1 to 5.0 percent by weight.

The hair coloring compositions according to the invention can be weakly acidic, neutral or alkaline according to their composition. The compositions typically have pH values of from 6.8 to 11.5. Their pH can be adjusted in the basic range with ammonia. Also, organic amines can be used for this purpose, including monoethanolamine and triethanolamine, or also inorganic bases, such as sodium hydroxide and potassium hydroxide. Inorganic or organic acids can be used for adjusting the pH in the acid range, for example phosphoric acid, acetic acid, citric acid or tartaric acid.

In order to use the oxidation hair coloring composition for dyeing hair one mixes the above-described hair coloring compositions according to the invention with an oxidizing agent immediately prior to use and applies a sufficient amount of the mixture to the hair, according to the hair abundance, generally from about 60 to 200 grams.

Typically hydrogen peroxide, or its addition compounds with urea, melamine, sodium borate or sodium carbonate, can be used in the form of a 3 to 12 percent, preferably 6 percent, aqueous solution as the oxidizing agent for developing the hair dye. Air oxygen can also be used as the oxidizing agent. If a 6 percent hydrogen peroxide solution is used as oxidizing agent, the weight ratio of hair coloring composition and oxidizing agent is 5:1 to 1:2, but preferably 1:1. The mixture of the oxidizing agent and the dye composition of the invention is allowed to act on the hair for about 10 to about 45 minutes, preferably about 30 minutes, at about 15 to 50 degrees Celsius, the hair is rinsed with water and dried. If necessary, it is washed with a shampoo and eventually after-rinsed with a weak organic acid, such as citric acid or tartaric acid. Subsequently the hair is dried.

The hair coloring composition according to the invention with a content of 2-arylaminomethyl-4-aminophenol compounds of Formula (1) as primary intermediate substances permits hair dyeing with outstanding color fastness, especially light fastness, fastness to washing and fastness to rubbing. The hair coloring composition according to the invention provides a broad palette of different color shades, which extend from blond to brown, purple, violet to blue and black shades, according to the type and composition of the dye compounds in it. Particularly the color shades produced have outstanding color intensity. The very good dyeing properties of the compositions according to the invention include the production of good color coverage and dyeing of virgin gray hair.

EXAMPLES 1 TO 35

Synthesis of 2-Arylaminomethyl-4-Aminophenol Compounds of Formula (1)

Following the general synthesis procedure outlined hereinbefore appropriate aromatic amines of the formula R—NH$_2$, wherein R is as defined hereinbefore, were reacted with brominated Wang polymer bound nitrobenzaldehyde of Formula (5) to produce the 2-arylaminomethyl-4-aminophenol Compound Nos. 1 to 35 set forth in Table 1. All compounds prepared were analyzed by HPLC and characterized by liquid chromatography mass spectrophotometer (LC/MS). The mass spectrophotometer used positive electron spray ionization (ESI) mode (ES$^+$) which measured the molecular weight of the products plus one hydrogen atom.

TABLE 1

| Compound No. | Molecular Structure | MW. Calcd | MW. Found ES+ | Purity(%) |
|---|---|---|---|---|
| 1 | 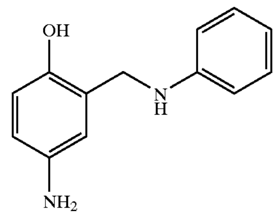 | 214.26933 | 215 | 92 |
| 2 | 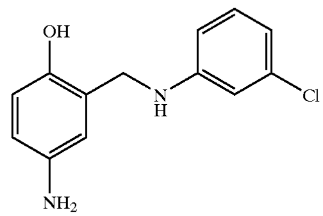 | 248.71436 | 249 | 97 |
| 3 | 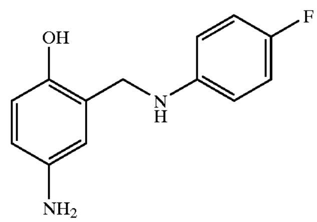 | 232.25976 | 233 | 95 |
| 4 | 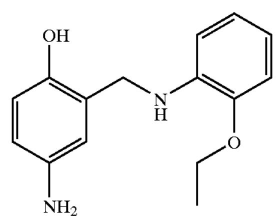 | 258.32291 | 259 | 92 |
| 5 | 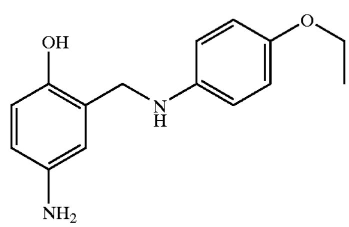 | 258.32291 | 259 | 76 |
| 6 | 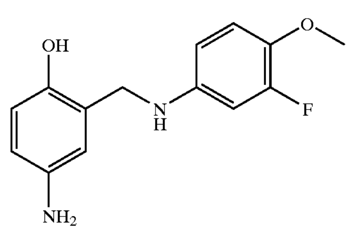 | 262.28625 | 263 | 95 |

TABLE 1-continued

| Compound No. | Molecular Structure | MW. Calcd | MW. Found ES+ | Purity(%) |
|---|---|---|---|---|
| 7 | 2-[(3-methoxyphenylamino)methyl]-4-aminophenol | 244.29582 | 245 | 97 |
| 8 | 2-[(3,4-dimethylphenylamino)methyl]-4-aminophenol | 242.32351 | 243 | 99 |
| 9 | 2-[(3-fluorophenylamino)methyl]-4-aminophenol | 232.25976 | 233 | 100 |
| 10 | 2-[(2-methoxy-5-methylphenylamino)methyl]-4-aminophenol | 258.32291 | 259 | 98 |
| 11 | 2-[(4-methoxy-2-methylphenylamino)methyl]-4-aminophenol | 258.32291 | 259 | 93 |
| 12 | 2-[(5-methoxy-2-methylphenylamino)methyl]-4-aminophenol | 258.32291 | 259 | 93 |

TABLE 1-continued

| Compound No. | Molecular Structure | MW. Calcd | MW. Found ES+ | Purity(%) |
|---|---|---|---|---|
| 13 | 2-hydroxy-5-amino-benzyl-NH-(3-cyanophenyl) | 239.27921 | 240 | 93 |
| 14 | 2-hydroxy-5-amino-benzyl-NH-(3-CF3-phenyl) | 282.26771 | 283 | 72 |
| 15 | 2-hydroxy-5-amino-benzyl-NH-(4-CF3-phenyl) | 282.26771 | 283 | 86 |
| 16 | 2-hydroxy-5-amino-benzyl-NH-(4,6-dimethylpyridin-2-yl) | 243.31109 | 244 | 98 |
| 17 | 2-hydroxy-5-amino-benzyl-NH-(3,4-dimethoxyphenyl) | 274.32231 | 275 | 100 |
| 18 | 2-hydroxy-5-amino-benzyl-NH-(4-hydroxyphenyl) | 230.26873 | 231 | 89 |

TABLE 1-continued

| Compound No. | Molecular Structure | MW. Calcd | MW. Found ES+ | Purity(%) |
|---|---|---|---|---|
| 19 | 2-hydroxy-5-amino-N-(4-ethylphenyl)benzylamine | 242.32351 | 243 | 98 |
| 20 | 2-hydroxy-5-amino-N-(4-hydroxy-2,5-dimethylphenyl)benzylamine | 258.32291 | 259 | 60 |
| 21 | 2-hydroxy-5-amino-N-(4-methoxyphenyl)benzylamine | 244.29582 | 245 | 95 |
| 22 | 2-hydroxy-5-amino-N-(2-chlorophenyl)benzylamine | 248.71436 | 249 | 93 |
| 23 | 2-hydroxy-5-amino-N-(4-methylphenyl)benzylamine | 228.29642 | 229 | 94 |
| 24 | 2-hydroxy-5-amino-N-(2-methylphenyl)benzylamine | 228.29642 | 229 | 97 |

TABLE 1-continued

| Compound No. | Molecular Structure | MW. Calcd | MW. Found ES+ | Purity(%) |
|---|---|---|---|---|
| 25 | 2-hydroxy-5-amino-benzyl-(2-methoxyphenyl)amine | 244.29582 | 245 | 93 |
| 26 | 2-hydroxy-5-amino-benzyl-(3-methylphenyl)amine | 228.29642 | 229 | 88 |
| 27 | 2-hydroxy-5-amino-benzyl-(4-propylphenyl)amine | 256.3506 | 257 | 98 |
| 28 | 2-hydroxy-5-amino-benzyl-(2,3-dimethylphenyl)amine | 242.32351 | 243 | 94 |
| 29 | 2-hydroxy-5-amino-benzyl-(2,5-dimethylphenyl)amine | 242.32351 | 243 | 91 |
| 30 | 2-hydroxy-5-amino-benzyl-(3,5-dimethylphenyl)amine | 242.32351 | 243 | 98 |

TABLE 1-continued

| Compound No. | Molecular Structure | MW. Calcd | MW. Found ES+ | Purity(%) |
|---|---|---|---|---|
| 31 | 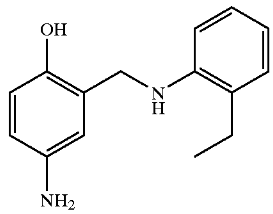 | 242.32351 | 243 | 98 |
| 32 | 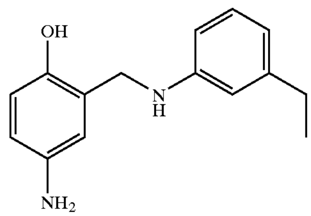 | 242.32351 | 243 | 98 |
| 33 | 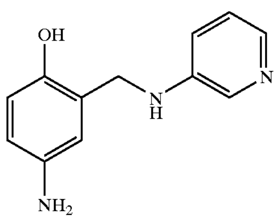 | 215.2547 | 216 | 93 |

EXAMPLES 34 TO 47

By the same synthesis route using appropriate aromatic amines of the formula $RNH_2$, the following 2-arylaminomethyl-4-aminophenol compounds are prepared when reacted with the brominated Wang polymer bound nitrobenzaldehyde 5: 5-methyl-4-amino-2-phenylaminomethyl-phenol; 5-methyoxy4-amino-2-phenylaminomethyl-phenol; 5-chloro4-amino-2-phenylaminomethyl-phenol; 4-amino-2-[(2-fluoro-phenylamino)-methyl]-phenol; 4-amino-2-[(2-hydroxy-phenylamino)-methyl]-phenol; 4-amino-2-[2-amino-phenylamino)-methyl]-phenol; 4-amino-2-[(2-trifluoromethyl-phenylamino)-methyl]-phenol; 4-amino-2-[(2-trifluoromethoxy-phenyl-amino)-methyl]-phenol; 2-(5-amino-2-hydroxy-benzylamino)-benzonitrile; 4-(5-amino-2-hydroxy-benzylamino)-benzonitrile; 4-amino-2-[(3,4-dihydroxy-phenylamino)-methyl]-phenol; 4-amino-2-[(4-amino-phenylamino methyl]-phenol; 4-amino-2-[(4-chloro-phenylamino)-methyl]-phenol; and 4-amino-2-[(4-trifluoromethoxy-phenylamino)-methyl]-phenol.

EXAMPLES 48 TO 80 AND

Comparative Examples A and B

Hair Coloring Compositions and Hair Dyeing Therewith

Hair coloring compositions 50 to 84 of this invention were prepared employing the 2-arylaminomethyl-4-aminophenol primary intermediates listed in Table 2. The hair coloring compositions formulated comprised the 2-arylaminomethyl-4-aminophenols and 2-methyl-5-aminophenol coupler in a concentration of 0.025 M in a base formulation of 7.85 g ethanol, 10 g sodium laureth sulfate, 0.3 g ascorbic acid, 0.3 g EDTA, 8.13 g 28% ammonium hydroxide and 73.5 g water. For comparison purposes hair coloring compositions employing 4-amino-2-methyl-phenol (2-MePAP) and 4-amino-3-methyl-phenol (3-MePAP) were also similar formulations and tested.

A mixture of the primary intermediate (1) (0.5 mL) and the coupler (0.5 mL) was mixed with 1 mL of 20 volume hydrogen peroxide. The mixture was applied to Piedmont hair tresses weighing from 700 to 900 mg mounted on a glass plate and then stored at 40° C. for 30 min, washed, shampooed, and dried. Color was evaluated using the Minolta Spectrophotometer CM-3700d (Table 1).

The Minolta 3700d spectrophotometer uses reflected light from a surface and gives results in terms of the CIE (International Commission on Illumination) tristimulus values. These values are subsequently transformed mathematically into the L* a* b* color space, wherein the magnitude of changes in hue and intensity of color correspond closely with those perceived by the human eye.

L*, being achromatic, ranges from black (L*=0) to white (L*=100); this term is called "metric lightness" and is a measure of how light or dark a color is, relative to a matching shade of gray. Hue is measured in terms of the chromaticity coordinates a* and b*, where a* indicates redness (a*>0) and b* indicates yellowness (b*>0). The values of a* and b* can be plotted with a* as the x-axis and b* as the y-axis to give quantitative color information: "metric chroma" is the length of a line from the origin (a*=0, b*=0) to the point of a sample reading while metric hue angle is the angle between the a* axis and the metric chroma line. Metric chroma indicates the strength of a color response (i.e., the extent to which a color differs from its matching shade of gray). Metric hue angle quantifies hue in degrees, with larger values indicating more yellow hues and smaller values indicating more red (or less yellow) hues.

A measure of the brightness of the coloration on the hair is Chroma C*, which is defined as $\sqrt{(a^*)^2+(b^*)^2}$, when the a* and b* values increase, the saturation of color increases, resulting in vivid color.

The results of the tests are set forth in the following Table 2. The baseline average values of L*, a* and b* for undyed, untreated Piedmont hair were L* 72.32, a* 2.0, b* 23.2.

The hair coloring results obtained are reported in Table 2.

TABLE 2

| Compound No. | Molecular Structure | L* | a* | b* | Chroma C* |
|---|---|---|---|---|---|
| 48 | 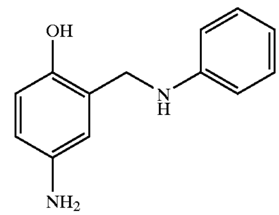 | 53.03 | 14.20 | 23.49 | 27.45 |
| 49 | 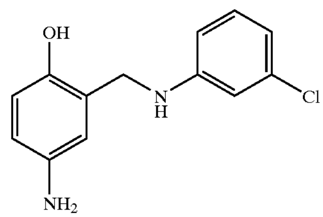 | 66.24 | 10.10 | 23.28 | 25.37 |
| 50 | 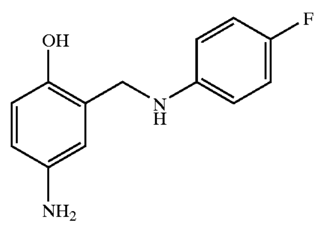 | 60.96 | 12.68 | 23.73 | 26.90 |
| 51 | 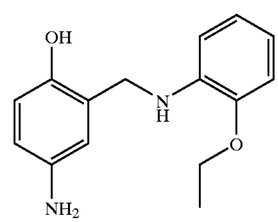 | 63.14 | 9.91 | 23.40 | 25.41 |
| 52 | 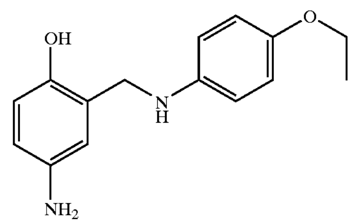 | 51.75 | 11.34 | 19.68 | 22.71 |
| 53 | 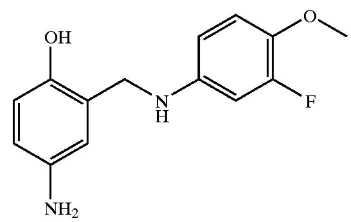 | 61.18 | 14.70 | 24.49 | 28.56 |

TABLE 2-continued

| Compound No. | Molecular Structure | L* | a* | b* | Chroma C* |
|---|---|---|---|---|---|
| 54 | 2-[(3-methoxyphenylamino)methyl]-4-aminophenol | 52.47 | 15.27 | 22.39 | 27.10 |
| 55 | 2-[(3,4-dimethylphenylamino)methyl]-4-aminophenol | 60.06 | 11.80 | 22.54 | 25.44 |
| 56 | 2-[(3-fluorophenylamino)methyl]-4-aminophenol | 52.36 | 14.70 | 22.19 | 26.61 |
| 57 | 2-[(2-methoxy-5-methylphenylamino)methyl]-4-aminophenol | 57.39 | 10.58 | 20.08 | 22.69 |
| 58 | 2-[(4-methoxy-2-methylphenylamino)methyl]-4-aminophenol | 59.48 | 13.29 | 23.55 | 27.04 |
| 59 | 2-[(5-methoxy-2-methylphenylamino)methyl]-4-aminophenol | 61.63 | 11.52 | 23.28 | 25.98 |

TABLE 2-continued

| Compound No. | Molecular Structure | L* | a* | b* | Chroma C* |
|---|---|---|---|---|---|
| 60 | 2-hydroxy-5-amino-benzyl-(3-cyanophenyl)amine | 56.31 | 17.16 | 26.37 | 31.46 |
| 61 | 2-hydroxy-5-amino-benzyl-(3-trifluoromethylphenyl)amine | 58.50 | 14.61 | 23.39 | 27.58 |
| 62 | 2-hydroxy-5-amino-benzyl-(4-trifluoromethylphenyl)amine | 63.63 | 13.34 | 23.55 | 27.06 |
| 63 | 2-hydroxy-5-amino-benzyl-(4,6-dimethylpyridin-2-yl)amine | 61.93 | 13.18 | 22.70 | 26.25 |
| 64 | 2-hydroxy-5-amino-benzyl-(3,4-dimethoxyphenyl)amine | 56.10 | 14.31 | 23.63 | 27.63 |
| 65 | 2-hydroxy-5-amino-benzyl-(4-hydroxyphenyl)amine | 58.22 | 16.49 | 27.72 | 32.25 |

TABLE 2-continued
| Compound No. | Molecular Structure | L* | a* | b* | Chroma C* |
|---|---|---|---|---|---|
| 66 | 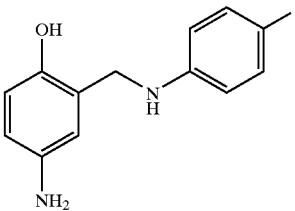 | 62.25 | 11.84 | 22.34 | 25.28 |
| 67 | 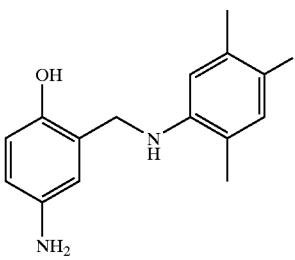 | 62.31 | 14.47 | 25.59 | 29.40 |
| 68 | 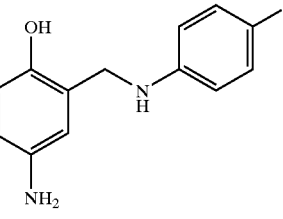 | 57.39 | 14.57 | 23.33 | 27.51 |
| 69 | 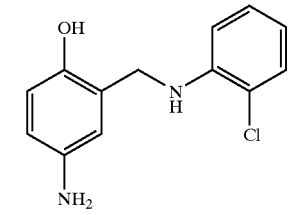 | 62.57 | 13.58 | 25.06 | 28.50 |
| 70 | 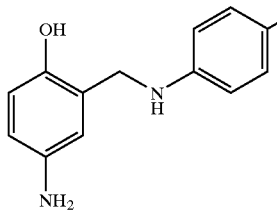 | 56.95 | 14.78 | 23.31 | 27.60 |
| 71 | 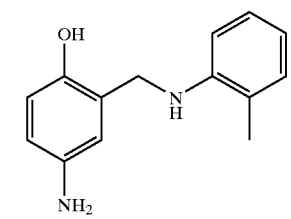 | 59.15 | 15.55 | 23.97 | 28.57 |

TABLE 2-continued
| Compound No. | Molecular Structure | L* | a* | b* | Chroma C* |
|---|---|---|---|---|---|
| 72 | 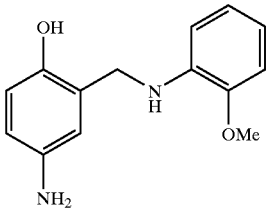 | 56.58 | 15.14 | 21.91 | 26.63 |
| 73 | 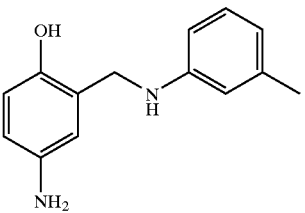 | 58.12 | 12.33 | 20.32 | 23.77 |
| 74 | 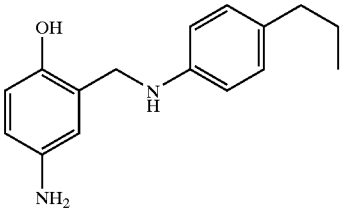 | 65.06 | 9.71 | 22.32 | 24.35 |
| 75 | 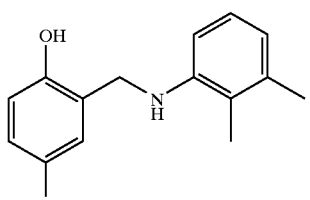 | 59.92 | 14.46 | 24.46 | 28.41 |
| 76 | 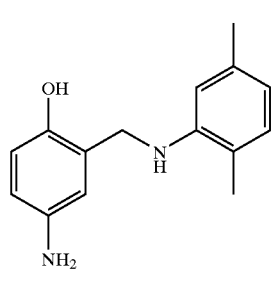 | 60.87 | 11.78 | 21.78 | 24.76 |
| 77 | 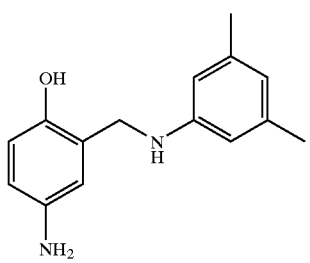 | 59.92 | 12.51 | 21.67 | 25.02 |

TABLE 2-continued

| Compound No. | Molecular Structure | L* | a* | b* | Chroma C* |
|---|---|---|---|---|---|
| 78 | (structure: 2-hydroxy-5-amino-benzyl-NH-(2-ethylphenyl)) | 60.73 | 15.02 | 23.08 | 27.54 |
| 79 | (structure: 2-hydroxy-5-amino-benzyl-NH-(3-ethylphenyl)) | 60.14 | 13.87 | 22.95 | 26.82 |
| 80 | (structure: 2-hydroxy-5-amino-benzyl-NH-(pyridin-3-yl)) | 55.21 | 18.21 | 25.13 | 31.03 |
| A | 2-MePAP | 56.72 | 17.45 | 23.40 | 29.19 |
| B | 3-MePAP | 55.53 | 19.91 | 21.01 | 28.94 |

Preferred combinations of hair coloring components employing a 2-arylaminomethyl-4-aminophenol primary intermediate of this invention are shown in combinations C1 to C136 in Tables A–H. Reading down the columns in Tables A–H, the Xes demonstrate combinations of dyes that can be formulated according to the present invention. For example, in Combination No. C10 in Column 5 of Table A, the 2-arylaminomethyl-4-aminophenol of Formula 1 of this invention, wherein R and $R^6$ are defined hereinbefore, can be combined with 2-amino-phenol and benzene-1,3-diol. Especially preferred as the 2-arylaminomethyl-4-aminophenol components in the combinations C1 to C136 of Tables A–H are 4-(5-amino-2-hydroxy-benzylamino)-benzonitrile, 4-amino-2-[(4-hydroxy-phenolamino)-methyl]-phenol, 4-amino-2-[4-hydroxy-2,5-dimethyl-phenyl-amino)-methyl]-phenol and 4-amino-2-(pyridin-3-ylaminomethyl)-phenol.

TABLE A

| Structure | IUPAC Name | Dye Combinations Name | C1 | C2 | C3 | C4 | C5 | C6 | C7 | C8 | C9 | C10 | C11 |
|---|---|---|---|---|---|---|---|---|---|---|---|---|---|
| (Formula with OH, $R^8$, NH-R, $NH_2$) | | 4-Amino-2-arylamino-methyl-phenol | x | x | x | x | x | x | x | x | x | x | x |
| (2-methyl-1,4-diaminobenzene structure) | 2-Methyl-benzene-1,4-diamine | p-Toluene-diamine | | | | | | | | | | | |

TABLE A-continued

Dye Combinations

| IUPAC Name | Name | C1 | C2 | C3 | C4 | C5 | C6 | C7 | C8 | C9 | C10 | C11 |
|---|---|---|---|---|---|---|---|---|---|---|---|---|
| Benzene-1,4-diamine | p-Phenylene-diamine | | | | | | | | | | | |
| 2-[(4-Amino-phenyl)-(2-hydroxy-ethyl)-amino]-ethanol | N,N-Bis(2-hydroxy-ethyl)-p-phenylene-diamine | | | | | | | | | | | |
| 1-(2,5-Diamino-phenyl)-ethanol | 1-Hydroxyethyl-p-phenylenediamine | | | | | | | | | | | |
| 4-Amino-3-methyl-phenol | 3-Methyl-p-aminophenol | | | | | | | | | | | |
| 2-Amino-phenol | o-Aminophenol | x | | | | | | | | | x | |
| Benzene-1,3-diol | Resorcinol | | x | | | | | | | | x | x |
| 2-Methyl-benzene-1,3-diol | 2-Methyl-resorcinol | | | x | | | | | | | | x |
| Naphthalen-1-ol | 1-Naphthol | | | | x | | | | | | | |
| 2-Methyl-naphthalen-1-ol | 2-Methyl-1-naphthol | | | | | x | | | | | | |
| 2-(2,4-Diamino-phenoxy)-ethanol | 2,4-Diamino-phenoxyethanol | | | | | | x | | | | | |
| Benzene-1,3-diamine | m-Phenylenediamine | | | | | | | x | | | | |

TABLE A-continued

| | | Dye Combinations | | | | | | | | | | | |
|---|---|---|---|---|---|---|---|---|---|---|---|---|---|
| Structure | IUPAC Name | Name | C1 | C2 | C3 | C4 | C5 | C6 | C7 | C8 | C9 | C10 | C11 |
| (3-aminophenol structure) | 3-Amino-phenol | m-Aminophenol | | | | | | | | | x | | |
| (5-amino-2-methylphenol structure) | 5-Amino-2-methyl-phenol | 2-Hydroxy-4-aminotoluene | | | | | | | | | | x | |
| (diaminopyrazole ethanol structure) | 2-(4,5-Diamino-pyrazol-1-yl)-ethanol | 1-Hydroxyethyl-4,5-diamono-pyrazole | | | | | | | | | | | |

TABLE B

| | Dye Combinations | | | | | | | | |
|---|---|---|---|---|---|---|---|---|---|
| Structure | C12 | C13 | C14 | C15 | C16 | C17 | C18 | C19 | C20 |
| (aminomethylphenol with R, R8 substituents) | x | x | x | x | x | x | x | x | x |
| (2-methyl-1,4-diaminobenzene) | | | | | | x | x | x | |
| (1,4-diaminobenzene) | | | | | | | | | |
| (N,N-bis(2-hydroxyethyl)-p-phenylenediamine) | | | | | | | | | |
| (1-(2,5-diaminophenyl)ethanol) | | | | | | | | | |
| (3-amino-4-methylphenol) | | | | | | | | | |

TABLE B-continued

Dye Combinations

| Structure | | | | | | | | | |
|---|---|---|---|---|---|---|---|---|---|
| 2-aminophenol (OH, NH₂) | | | | | | | x | | |
| resorcinol (1,3-dihydroxybenzene) | x | x | x | x | x | x | | x | |
| 2-methylresorcinol | | | | | | | | x | |
| 1-naphthol | x | | | | | | | | |
| 2-methyl-1-naphthol | | x | | | | | | | |
| 2,4-diamino-1-(2-hydroxyethoxy)benzene | | | x | | | | | | |
| m-phenylenediamine | | | | x | | | | | |
| 3-aminophenol | | | | | x | | | | |
| 5-amino-2-methylphenol | | | | | | x | | | |
| 4,5-diamino-1-(2-hydroxyethyl)pyrazole | | | | | | | | | |

TABLE B-continued
Dye Combinations
| Structure | C21 | C22 | C23 | C24 | C25 | C26 | C27 | C28 | C29 |
|---|---|---|---|---|---|---|---|---|---|
| 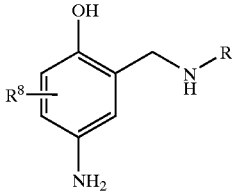 | x | x | x | x | x | x | x | x | x |
| 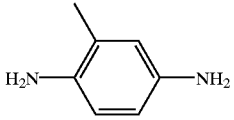 | x | x | x | x | x | x | x | x | x |
| 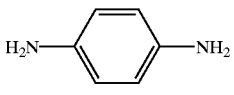 | | | | | | | | | |
| 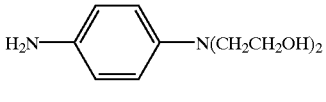 | | | | | | | | | |
| 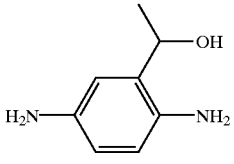 | | | | | | | | | |
| 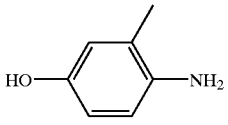 | | | | | | | | | |
| 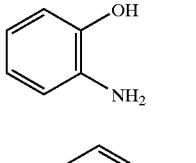 | | | | | | x | | | |
| 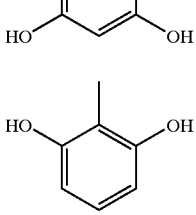 | | | | | | | x | x | x |
| 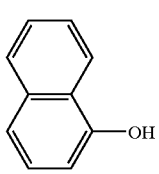 | | | | | | | | x | |
|  | | x | | | | | | | x |

TABLE B-continued

Dye Combinations

| Structure | |
|---|---|
| 1-hydroxy-2-methylnaphthalene | x |
| 2,4-diamino-1-(2-hydroxyethoxy)benzene | x |
| 1,3-diaminobenzene | x |
| 3-aminophenol | x |
| 5-amino-2-methylphenol | x |
| 4,5-diamino-1-(2-hydroxyethyl)pyrazole | |

TABLE C

Dye Combinations

| Structure | C30 | C31 | C32 | C33 | C34 | C35 | C36 | C37 | C38 |
|---|---|---|---|---|---|---|---|---|---|
| 2-hydroxy-5-amino-benzylamine derivative (with $R^8$, R) | x | x | x | x | x | x | x | x | x |
| 2-methyl-1,4-diaminobenzene | x | x | x | x | x | | | | |
| 1,4-diaminobenzene | | | | | | x | x | x | x |
| $H_2N$-C$_6$H$_4$-$N(CH_2CH_2OH)_2$ | | | | | | | | | |

TABLE C-continued

Dye Combinations

| Structure | | | | | | | | | |
|---|---|---|---|---|---|---|---|---|---|
| 2,5-diamino-(1-hydroxyethyl)benzene | | | | | | | | | |
| 4-hydroxy-2-methylaniline | | | | | | | | | |
| 2-aminophenol | | | | | | x | | | |
| resorcinol | x | x | x | x | x | | x | | |
| 2-methylresorcinol | | | | | | | | x | |
| 1-naphthol | | | | | | | | | x |
| 2-methyl-1-naphthol | x | | | | | | | | |
| 2,4-diamino-1-(2-hydroxyethoxy)benzene | x | | | | | | | | |
| m-phenylenediamine | | | | | x | | | | |
| 3-aminophenol | | | | | | x | | | |
| 5-amino-2-methylphenol | | | | | | | x | | |

TABLE C-continued

Dye Combinations

[Structure: 5-amino-4-amino-1-(2-hydroxyethyl)pyrazole]

| Structure | C39 | C40 | C41 | C42 | C43 | C44 | C45 | C46 | C47 |
|---|---|---|---|---|---|---|---|---|---|
| [2-hydroxy-5-amino-benzyl amine with R, R⁸ substituents] | x | x | x | x | x | x | x | x | x |
| [2-methyl-1,4-phenylenediamine] | | | | | | | | | |
| [1,4-phenylenediamine] | x | x | x | x | x | x | x | x | x |
| [N,N-bis(2-hydroxyethyl)-p-phenylenediamine] | | | | | | | | | |
| [2,5-diamino-α-methylbenzyl alcohol] | | | | | | | | | |
| [4-amino-3-methylphenol] | | | | | | | | | |
| [2-aminophenol] | | | | | | | x | | |
| [resorcinol] | | | | | | x | x | x | x |
| [2-methylresorcinol] | | | | | | | x | | |

TABLE C-continued

Dye Combinations

| Structure | | | | | | | | |
|---|---|---|---|---|---|---|---|---|
| 1-naphthol (naphthalene with OH) | | | | | | | x | |
| 2-methyl-1-naphthol (naphthalene with OH and CH₃) | x | | | | | | | x |
| 2,4-diamino-1-(2-hydroxyethoxy)benzene ($H_2N$–C₆H₃($NH_2$)–$OCH_2CH_2OH$) | | x | | | | | | |
| 1,3-diaminobenzene ($H_2N$–C₆H₄–$NH_2$) | | | x | | | | | |
| 3-aminophenol (HO–C₆H₄–$NH_2$) | | | | x | | | | |
| 5-amino-2-methylphenol ($H_2N$–C₆H₃(CH₃)–OH) | | | | | x | | | |
| 4,5-diamino-1-(2-hydroxyethyl)pyrazole | | | | | | | | |

TABLE D

| Structure | Dye Combinations | | | | | | | | | | | |
|---|---|---|---|---|---|---|---|---|---|---|---|---|
| | C48 | C49 | C50 | C51 | C52 | C53 | C54 | C55 | C56 | C57 | C58 | C59 |
| 2-aminomethyl-4-amino-phenol derivative (with OH, $R^6$, $NH-R$, $NH_2$) | x | x | x | x | x | x | x | x | x | x | x | x |
| 2-methyl-1,4-diaminobenzene ($H_2N$–C₆H₃(CH₃)–$NH_2$) | | | | | | | | | | | | |

TABLE D-continued

| Structure | | | | | | | | | | | |
|---|---|---|---|---|---|---|---|---|---|---|---|
| H2N—⌬—NH2 (p-phenylenediamine) | x | x | x | x | | | | | | | |
| H2N—⌬—N(CH2CH2OH)2 | | | | | | | | | | | |
| 2,5-diaminophenylethanol | | | | | x | x | x | x | x | x | x | x |
| 4-amino-3-methylphenol | | | | | | | | | | | | |
| 2-aminophenol | | | | | x | | | | | | | |
| resorcinol | x | x | x | x | | x | | | | | | |
| 2-methylresorcinol | | | | | | | | x | | | | |
| 1-naphthol | | | | | | | | x | | | | |
| 2-methyl-1-naphthol | | | | | | | | | | x | | |
| 2,4-diamino-1-(β-hydroxyethyloxy)benzene | | x | | | | | | | | x | | |
| m-phenylenediamine | | | x | | | | | | | x | | |

TABLE D-continued

| Structure | | | | | | |
|---|---|---|---|---|---|---|
| 3-aminophenol (HO-C6H4-NH2) | x | | | | x | |
| 5-amino-2-methylphenol (H2N-C6H3(CH3)-OH) | x | | | | | |
| 4,5-diamino-1-(2-hydroxyethyl)pyrazole | | | | | | |

| | Dye Combinations | | | | | |
|---|---|---|---|---|---|---|
| Structure | C60 | C61 | C62 | C63 | C64 | C65 |
| 2-hydroxy-5-amino-benzylamine (R6, R substituted) | x | x | x | x | x | x |
| 2,5-diamino-toluene | | | | | | |
| 1,4-phenylenediamine | | | | | | |
| N,N-bis(2-hydroxyethyl)-1,4-phenylenediamine | | | | | | |
| 1-(2,5-diaminophenyl)ethanol | x | x | x | x | x | x |
| 4-amino-3-methylphenol | | | | | | |
| 2-aminophenol | | | x | | | |
| resorcinol | | x | x | x | x | x |

TABLE D-continued

[Structure: 2-methylbenzene-1,3-diol (HO, CH₃, OH)] — x

[Structure: 1-naphthol] — x

[Structure: 2-methyl-1-naphthol] — x

[Structure: 2-amino-4-aminophenyl-OCH₂CH₂OH; H₂N, NH₂, OCH₂CH₂OH] — x

[Structure: 1,3-diaminobenzene; H₂N, NH₂]

[Structure: 3-aminophenol; HO, NH₂]

[Structure: 5-amino-2-methylphenol; H₂N, CH₃, OH] — x

[Structure: pyrazole with NH₂, H₂N, N-CH₂CH₂OH]

TABLE E

| Structure | Dye Combinations | | | | | | | | | | | |
|---|---|---|---|---|---|---|---|---|---|---|---|---|
| | C66 | C67 | C68 | C69 | C70 | C71 | C72 | C73 | C74 | C75 | C76 | C77 |
| [Structure: OH, R⁶, CH₂NHR, NH₂] | x | x | x | x | x | x | x | x | x | x | x | x |

TABLE E-continued

| Structure | | | | |
|---|---|---|---|---|
| 2-methyl-1,4-diaminobenzene | | | | |
| 1,4-diaminobenzene | | | | |
| N,N-bis(2-hydroxyethyl)-1,4-diaminobenzene | | | | |
| 1-(2,5-diaminophenyl)ethanol | x | x | x | |
| 4-amino-3-methylphenol | | | | |
| 2-aminophenol | | x | | |
| resorcinol | x | x | x | x |
| 2-methylresorcinol | | | x | |
| 1-naphthol | | | x | |
| 2-methyl-1-naphthol | | | x | |
| 2,4-diamino-1-(2-hydroxyethoxy)benzene | | | x | |

TABLE E-continued

| Structure | | | | | | |
|---|---|---|---|---|---|---|
| 1,3-diaminobenzene (H₂N-C₆H₄-NH₂) | x | | | | x | |
| 3-aminophenol (HO-C₆H₄-NH₂) | x | | | | | x |
| 5-amino-2-methylphenol (H₂N-C₆H₃(CH₃)-OH) | x | | | | | x |
| 4,5-diamino-1-(2-hydroxyethyl)pyrazole | x | x | x | x | x | x | x | x | x |

| | Dye Combinations | | | | | |
|---|---|---|---|---|---|---|
| Structure | C78 | C79 | C80 | C81 | C82 | C83 |
| 2-(aminomethyl-NHR)-4-amino-phenol with R⁶ | x | x | x | x | x | x |
| 2-methyl-1,4-diaminobenzene | | | | | | |
| 1,4-diaminobenzene | | | | | | |
| N,N-bis(2-hydroxyethyl)-1,4-phenylenediamine | | | | | | |
| 1-(2,5-diaminophenyl)ethanol | | | | | | |
| 4-amino-3-methylphenol | | | | | | |
| 2-aminophenol | x | | | | | |

TABLE E-continued

| Structure | | | | | | |
|---|---|---|---|---|---|---|
| resorcinol (1,3-dihydroxybenzene) | x | x | x | x | x | x |
| 2-methylresorcinol | | | x | | | |
| 1-naphthol | | | | x | | |
| 2-methyl-1-naphthol | | | | x | | |
| 4-(2-hydroxyethoxy)-1,3-phenylenediamine | | | | | x | |
| 1,3-phenylenediamine | | | | | | x |
| 3-aminophenol | | | | | | |
| 5-amino-2-methylphenol | | | | | | |
| 4,5-diamino-1-(2-hydroxyethyl)pyrazole | x | x | x | x | x | x |

TABLE F

| Structure | Dye Combinations | | | | | | | | | | | |
|---|---|---|---|---|---|---|---|---|---|---|---|---|
| | C84 | C85 | C86 | C87 | C88 | C89 | C90 | C91 | C92 | C93 | C94 | C95 |
| OH / R$^6$—benzene—CH$_2$NHR / NH$_2$ | x | x | x | x | x | x | x | x | x | x | x | x |
| 2-methyl-1,4-diaminobenzene (H$_2$N—C$_6$H$_3$(CH$_3$)—NH$_2$) | | | x | x | x | x | x | x | x | x | x | |
| H$_2$N—C$_6$H$_4$—NH$_2$ | | | | | | | | | | | x | |
| H$_2$N—C$_6$H$_4$—N(CH$_2$CH$_2$OH)$_2$ | | | | | | | | | | | | |
| 2,5-diamino-α-methylbenzyl alcohol | | | | | | | | | | | | |
| 4-hydroxy-2-methylaniline | | | | | | | | | | | | |
| 2-aminophenol | | | | x | | | | | | | x | |
| resorcinol | | x | x | | x | | | | | | | |
| 2-methylresorcinol | | | | | | | x | | | | | |
| 1-naphthol | | | | | | | x | | | | | |

TABLE F-continued
| Structure | | | | | | | | | | | | |
|---|---|---|---|---|---|---|---|---|---|---|---|---|
| 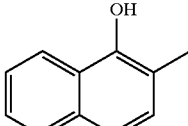 | | | | | | | | | | x | | |
| 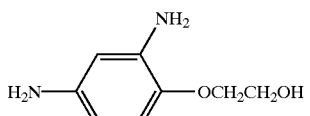 | | | | | | | | | | | x | |
| 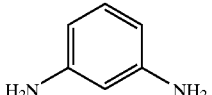 | | | | | | | | | x | | | |
| 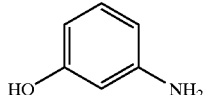 | x | | | | | | | | | x | | |
| 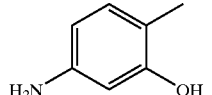 | | | x | | | | | | | | | x |
| 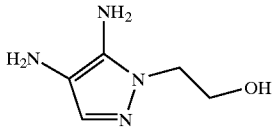 | x | x | x | x | x | x | x | x | x | x | x | x |
| | Dye Combinations | | | | | |
|---|---|---|---|---|---|---|
| Structure | C96 | C97 | C98 | C99 | C100 | C101 |
| 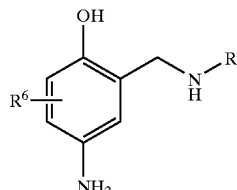 | x | x | x | x | x | x |
| 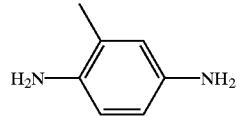 | | | | | | |
| 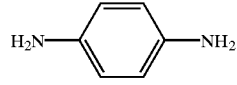 | x | x | x | x | x | x |
| 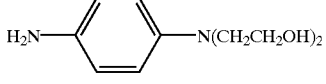 | | | | | | |
| 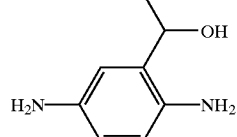 | | | | | | |

TABLE F-continued
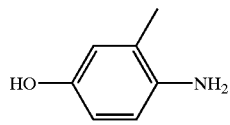
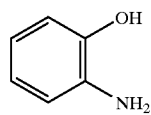
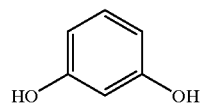                                          x
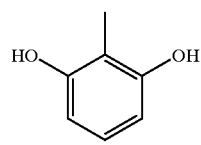                                          x
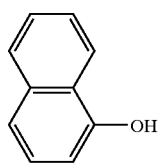                                          x
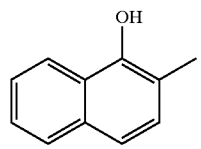                                          x
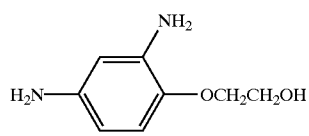                                          x
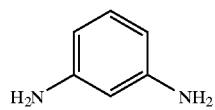                                          x
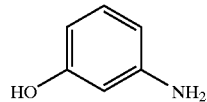
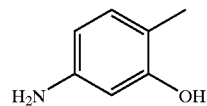
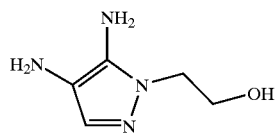      x     x     x     x     x     x

TABLE G

| Structure | Dye Combinations |||||||||||| 
| --- | --- | --- | --- | --- | --- | --- | --- | --- | --- | --- | --- | --- |
| | C102 | C103 | C104 | C105 | C106 | C107 | C108 | C109 | C110 | C111 | C112 | C113 |
| 2-(aminomethyl)-4-aminophenol ($R^6$, R substituted) | x | x | x | x | x | x | x | x | x | x | x | x |
| 2-methyl-1,4-phenylenediamine | | | | | | | | | | | x | |
| 1,4-phenylenediamine | x | x | | | | | | | | | | |
| N,N-bis(2-hydroxyethyl)-p-phenylenediamine | | | | | | | | | | | | |
| 1-(2,5-diaminophenyl)ethanol | | | x | x | x | x | x | x | x | x | x | |
| 4-amino-3-methylphenol | | | | | | | | | | | | |
| 2-aminophenol | | | x | | | | | | | | x | |
| resorcinol | | | x | | | | | | | | x | |
| 2-methylresorcinol | | | | | x | | | | | | | |
| 1-naphthol | | | | | x | | | | | | | |

TABLE G-continued
| Structure | | | | | | | | | | | | |
|---|---|---|---|---|---|---|---|---|---|---|---|---|
| 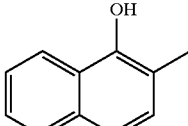 | | | | | | | | x | | | | |
| 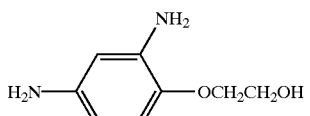 | | | | | | | | | x | | | |
| 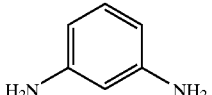 | | | | | | | | | | x | | |
| 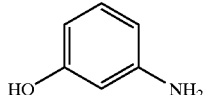 | | x | | | | | | | | | x | |
| 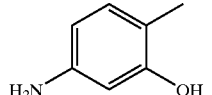 | | | x | | | | | | | | | x |
| 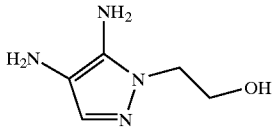 | x | x | x | x | x | x | x | x | x | x | x | x |
| | Dye Combinations | | | | | |
|---|---|---|---|---|---|---|
| Structure | C114 | C115 | C116 | C117 | C118 | C119 |
| 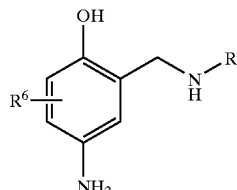 | x | x | x | x | x | x |
| 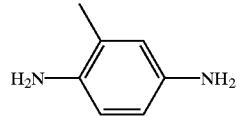 | x | x | x | x | x | x |
| 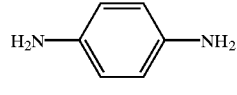 | | | | | | |
| 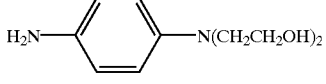 | | | | | | |
| 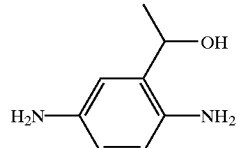 | | | | | | |

TABLE G-continued
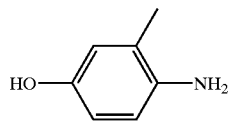
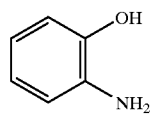
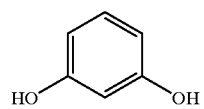   x   x   x   x   x   x
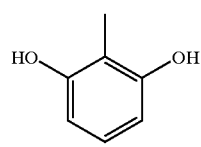   x
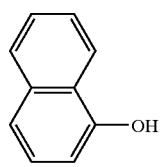   x
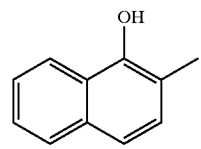   x
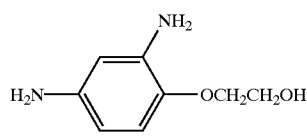   x
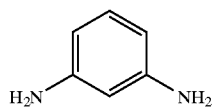   x
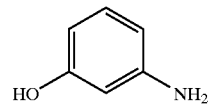   x
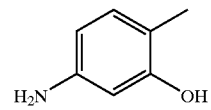
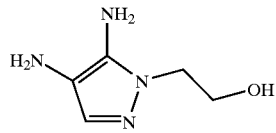   x   x   x   x   x   x

TABLE H

| Structure | Dye Combinations |||||||||||
|---|---|---|---|---|---|---|---|---|---|---|---|
| | C120 | C121 | C122 | C123 | C124 | C125 | C126 | C127 | C128 | C129 | C130 |
| 2-aminomethyl-4-aminophenol (with R, R⁶) | x | x | x | x | x | x | x | x | x | x | x |
| 2-methyl-1,4-phenylenediamine | | x | | | | | | | | | |
| 1,4-phenylenediamine | | | x | x | x | x | x | x | x | x | |
| N,N-bis(2-hydroxyethyl)-p-phenylenediamine | | | | | | | | | | | |
| 2,5-diamino-α-methylbenzyl alcohol | | | | | | | | | x | x | |
| 2-methyl-4-aminophenol | | | | | | | | | | | |
| 2-aminophenol | | | x | | | | | | x | | |
| resorcinol | x | x | x | x | x | x | x | x | x | x | x |
| 2-methylresorcinol | | | | x | | | | | | x | |
| 1-naphthol | | | | x | | | | | | | |

TABLE H-continued
| Structure | | | | | | | | | | | |
|---|---|---|---|---|---|---|---|---|---|---|---|
| 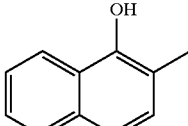 | | | | | x | | | | | | |
| 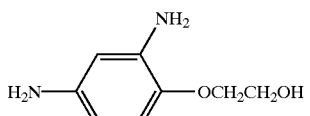 | | | | | | x | | | | | |
| 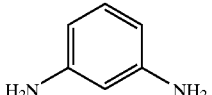 | | | | | | | x | | | | |
| 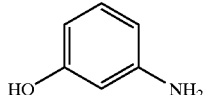 | | | | | | | | x | | | |
| 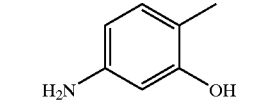 | x | | | | | | | | x | | |
| 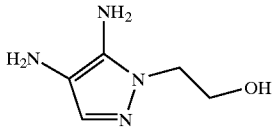 | x | x | x | x | x | x | x | x | x | x | x |
| | Dye Combinations | | | | | |
|---|---|---|---|---|---|---|
| Structure | C131 | C132 | C133 | C134 | C135 | C136 |
| 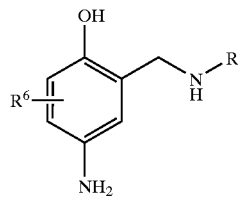 | x | x | x | x | x | x |
| 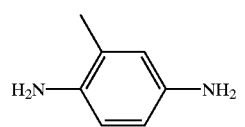 | | | | | | |
| 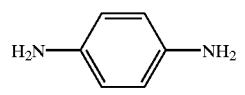 | | | | | | |
| 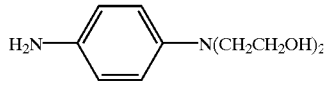 | | | | | | |
| 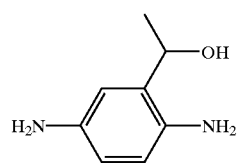 | x | x | x | x | x | x |

TABLE H-continued
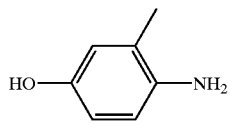
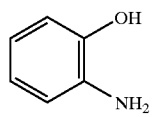
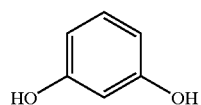     x   x   x   x   x   x
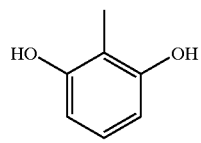
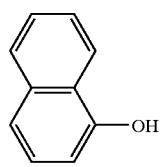     x
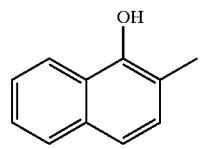     x
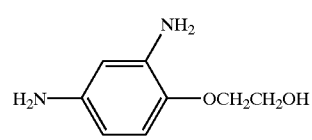     x
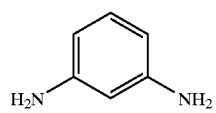       x
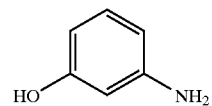         x
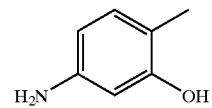           x
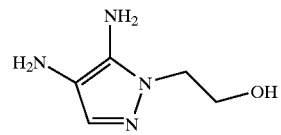   x   x   x   x   x   x

We claim:
1. A 2-arylaminomethyl-4-aminophenol compound of Formula (1):

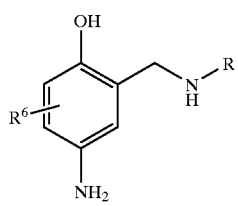
(1)

wherein R is a moiety selected from formulae (2), (3) or (4)

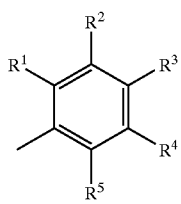
(2)

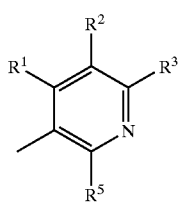
(3)

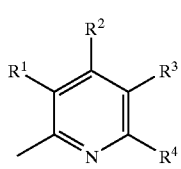
(4)

wherein $R^1$, $R^2$, $R^3$, $R^4$ and $R^5$ are each independently selected from the group consisting of a hydrogen atom, a halogen atom, a hydroxy group, an amino group, a $C_1$–$C_6$ alkyl group, $C_1$–$C_6$ haloalkyl group, a $C_1$–$C_6$ alkoxy group, $C_1$–$C_6$ haloalkoxy group and a nitrile group; and $R^6$ is selected from the group consisting of a hydrogen atom, a halogen atom, a $C_1$–$C_4$ alkyl and a $C_1$–$C_4$ alkoxy group.

2. A 2-arylaminomethyl-4-aminophenol of claim 1 wherein $R^6$ is hydrogen; $R^1$ and $R^5$ are each independently selected from the group consisting of hydrogen methyl, ethyl, methoxy, ethoxy, or chlorine; $R^2$ and $R^4$ are each independently hydrogen, chlorine, fluorine, methyl, ethyl, methoxy, trifluoromethyl, or trifluoromethoxy; and $R^3$ is selected from the group consisting of hydrogen, hydroxy, fluorine, methyl, ethyl, propyl, methoxy, ethoxy or trifluoromethyl.

3. A 2-arylaminomethyl-4-aminophenol of claim 1 comprising 4-(5-amino-2-hydroxy-benzylamino)-benzonitrile.

4. A 2-arylaminomethyl-4-aminophenol of claim 1 comprising 4-amino-2-[(4-hydroxy-phenylamino)-methyl]-phenol.

5. A 2-arylaminomethyl-4-aminophenol of claim 1 comprising 4-amino-2-[4-hydroxy-2,5-dimethyl-phenylamino)-methyl]-phenol.

6. A 2-arylaminomethyl-4-aminophenol of claim 1 comprising 4-amino-2-(pyridin-3-ylaminomethyl)-phenol.

7. In a hair coloring system comprising a composition containing one or more oxidative hair coloring agents and a composition containing one or more oxidizing agents, the improvement comprising the presence of a 2-arylaminomethyl-4-aminophenol compound of claim 1 as a primary intermediate in the composition containing the one or more oxidative hair coloring agents.

8. A hair coloring system according to claim 7 wherein the composition comprising one or more oxidative hair coloring agents additionally comprises one or more primary intermediate selected from the group consisting of: 2-methyl-benzene-1,4-diamine, benzene-1,4-diamine, 2-(2,5-diamino-phenyl)-ethanol, 1-(2,5-diamino-phenyl)-ethanol, 2-[(4-amino-phenyl)-(2-hydroxy-ethyl)-amino]-ethanol, 4-amino-phenol, 4-methylamino-phenol, 4-amino-3-methyl-phenol, 1-(5-amino-2-hydroxy-phenyl)-ethane-1,2-diol, 2-amino-phenol, 2-amino-5-methyl-phenol, 2-amino-6-methyl-phenol, N-(4-amino-3-hydroxy-phenyl)-acetamide, pyrimidine-2,4,5,6-tetramine and 2-(4,5-diamino-1H-pyrazol-1-yl)ethanol.

9. A hair coloring system according to claim 7 wherein the composition comprising one or more oxidative hair coloring agents additionally comprises one or more couplers selected from the group consisting of: benzene-1,3diol, 4-chlorobenzene-1,3-diol, naphthalen-1-ol, 2-methyl-naphthalen-1-ol, 2-methyl-benzene-1,3-diol, 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, 3-(2,4-diamino-phenoxy)-propan-1-ol, 3-amino-phenol, 5-amino-2-methyl-phenol, 5-(2-hydroxy-ethylamino)-2-methyl-phenol, and 3-amino-2-methyl-phenol, 3,4-dihydro-2H-1,4-benzoxazin-6-ol, 4-methyl-2-phenyl-2,4-dihydro-3H-pyrazol-3-one, and 1H-indol-6-ol, and 2-aminopyridin-3-ol.

10. A hair coloring system according to claim 7 wherein the 2-arylaminomethyl-4-aminophenol compound comprises 4-(5-amino-2-hydroxy-benzylamino)-benzonitrile.

11. A hair coloring system according to claim 7 wherein the 2-arylaminomethyl-4-aminophenol compound comprises 4-amino-2-[(4-hydroxy-phenolamino)-methyl]-phenol.

12. A hair coloring system according to claim 7 wherein the 2-arylaminomethyl-4-aminophenol compound comprises 4-amino-2-[4-hydroxy-2,5-dimethylphenylamino)-methyl]-phenol.

13. A hair coloring system according to claim 7 wherein the 2-arylaminomethyl-4-aminophenol compound comprises 4-amino-2-(pyridin-3-ylaminomethyl)-phenol.

14. In a system for coloring hair wherein at least one primary intermediate is reacted with at least one coupler in the presence of an oxidizing agent to produce an oxidative hair dye, the improvement wherein a 2-arylaminomethyl-4-aminophenol of claim 1 is employed as a primary intermediate.

15. A system for coloring hair according to claim 14 wherein the system additionally comprises one or more primary intermediates selected from the group consisting of: 2-methyl-benzene-1,4-diamine, benzene-1,4-diamine, 2-(2,5-diamino-phenyl)-ethanol, 1-(2,5-diamino-phenyl)-ethanol, 2-[(4-amino-phenyl)-(2-hydroxy-ethyl)-amino]-ethanol, 4-amino-phenol, 4-methylamino-phenol, 4-amino-3-methyl-phenol, 1-(5-amino-2-hydroxy-phenyl)-ethane-1,2-diol, 2-amino-phenol, 2-amino-5-methyl-phenol, 2-amino-6-methyl-phenol, N-(4-amino-3-hydroxy-phenyl)-acetamide, pyrimidine-2,4,5,6-tetramine and 2-(4,5-diamino-1H-pyrazol-1-yl)ethanol.

16. A system for coloring hair according to claim 14 wherein the system additionally comprises one or more couplers selected from the group consisting of: benzene-1,3-diol, 4-chlorobenzene-1,3-diol, naphthalen-1-ol, 2-methyl-naphthalen-1-ol, 2-methyl-benzene-1,3-diol, 2-(2,4-diamino-phenoxy)-ethanol, 2-(3-amino4-methoxy-phenylamino)-ethanol, 2-[2,4-diamino-5-(2-hydroxy-ethoxy)-phenoxy]-ethanol, 3-(2,4-diamino-phenoxy)-propan-1-ol, 3-amino-phenol, 5-amino-2-methyl-phenol, 5-(2-hydroxy-ethylamino)-2-methyl-phenol, 3-amino-2-methyl-phenol, 3,4-dihydro-2H-1,4-benzoxazin-6-ol, 4-methyl-2-phenyl-2,4-dihydro-3H-pyrazol-3-one, 1H-indol-6-ol, and 2-aminopyridin-3-ol.

17. A system for coloring hair according to claim 14 wherein the system additionally comprises one or more primary intermediates selected from the group consisting of: 2-methyl-benzene-1,4-diamine, benzene-1,4-diamine, 2-(2,5-diamino-phenyl)-ethanol, 1-(2,5-diamino-phenyl)-ethanol, 2-[(4-amino-phenyl)-(2-hydroxy-ethyl)-amino]-ethanol, 4-amino-phenol, 4-methylamino-phenol, 4-amino-3-methyl-phenol, 1-(5-amino-2-hydroxy-phenyl)-ethane-1,2-diol, 2-amino-phenol, 2-amino-5-methyl-phenol, 2-amino-6-methyl-phenol, N-(4-amino-3-hydroxy-phenyl)-acetamide, pyrimidine-2,4,5,6-tetramine and 2-(4,5-diamino-1H-pyrazol-1-yl)ethanol and one or more couplers selected from the group consisting of: benzene-1,3-diol, 4-chlorobenzene-1,3-diol, naphthalen-1-ol, 2-methyl-naphthalen-1-ol, 2-methyl-benzene-1,3-diol, 2-(2,4-diamino-phenoxy)-ethanol, 2-(3-amino4-methoxy-phenylamino)-ethanol, 2-[2,4-diamino-5-(2-hydroxy-ethoxy)-phenoxy]-ethanol, 3-(2,4-diamino-phenoxy)-propan-1-ol, 3-amino-phenol, 5-amino-2-methyl-phenol, 5-(2-hydroxy-ethylamino)-2-methyl-phenol, 3-amino-2-methyl-phenol, 3,4-dihydro-2H-1,4-benzoxazin-6-ol, 4-methyl-2-phenyl-2,4-dihydro-3H-pyrazol-3-one, 1H-indol-6-ol, and 2-aminopyridin-3-ol.

18. A hair coloring composition for dyeing human hair comprising, in a suitable carrier or vehicle, a dyeing effective amount of:
   (a) at least one primary intermediate comprising a 2-arylaminomethyl-4-aminophenol of claim 1,
   (b) at least one coupler, and
   (c) at least one oxidizing agent.

19. A hair coloring composition according to claim 18 wherein the 2-arylaminomethyl-4-aminophenol compound comprises 4-(5-amino-2-hydroxy-benzylamino)-benzonitrile.

20. A hair coloring composition according to claim 18 wherein the 2-arylaminomethyl-4-aminophenol compound comprises 4-amino-2-[(4-hydroxy-phenolamino)-methyl]-phenol.

21. A hair coloring composition according to claim 18 wherein the 2-arylaminomethyl-4-aminophenol compound comprises 4-amino-2-[4-hydroxy-2,5-dimethyl-phenylamino)-methyl]-phenol.

22. A hair coloring composition according to claim 18 wherein the 2-arylaminomethyl-4-aminophenol compound comprises 4-amino-2-(pyridin-3-ylaminomethyl)-phenol.

23. A process for dyeing human hair comprising applying a dyeing effective amount of a hair coloring composition of claim 18 to the hair and permitting the composition to contact the hair for a dyeing effective period of time, and then rinsing, shampooing and drying the hair.

24. A process for dyeing human hair comprising applying a dyeing effective amount of a hair coloring composition of claim 19 to the hair and permitting the composition to contact the hair for a dyeing effective period of time, and then rinsing, shampooing and drying the hair.

25. A process for dyeing human hair comprising applying a dyeing effective amount of a hair coloring composition of claim 20 to the hair and permitting the composition to contact the hair for a dyeing effective period of time, and then rinsing, shampooing and drying the hair.

26. A process for dyeing human hair comprising applying a dyeing effective amount of a hair coloring composition of claim 21 to the hair and permitting the composition to contact the hair for a dyeing effective period of time, and then rinsing, shampooing and drying the hair.

27. A process for dyeing human hair comprising applying a dyeing effective amount of a hair coloring composition of claim 22 to the hair and permitting the composition to contact the hair for a dyeing effective period of time, and then rinsing, shampooing and drying the hair.

\* \* \* \* \*